United States Patent [19]
Jaehne et al.

[11] Patent Number: 6,090,833
[45] Date of Patent: Jul. 18, 2000

[54] POLYCYCLIC DIHYDROTHIAZOLES, THEIR PREPARATION, AND USE AS PHARMACEUTICALS

[75] Inventors: Gerhard Jaehne, Frankfurt; Heiner Glombik, Hofheim; Karl Geisen, Frankfurt; Martin Bickel, Bad Homburg, all of Germany

[73] Assignee: Aventis Pharma Deutschand GmbH, Germany

[21] Appl. No.: 09/406,855

[22] Filed: Sep. 29, 1999

[30] Foreign Application Priority Data

Sep. 29, 1998 [DE] Germany ............................ 198 44 547

[51] Int. Cl.$^7$ ...................... A61K 31/428; C07D 277/60; C07D 417/06
[52] U.S. Cl. ........................ 514/366; 514/338; 546/270.1; 548/150
[58] Field of Search ...................... 548/150; 546/270.1; 514/338, 366

[56] References Cited

U.S. PATENT DOCUMENTS 2,942,003   6/1960   Copeland ................................. 260/304

FOREIGN PATENT DOCUMENTS

| 0 749 966 | 12/1996 | European Pat. Off. . |
| 26 40 358 | 3/1978 | Germany . |
| 97/08159 | 3/1997 | WIPO . |
| 98/13356 | 4/1998 | WIPO . |

OTHER PUBLICATIONS

Hashem M.M. et al., "Novel pyrazolo, isoxazolo, and thiazolo steroidal systems and model analogs containing dimethoxylaryl (or dihydroxylaryl) groups and derivatives. Synthesis, spectral properties, and biological activity", J. of Med. Chem. vol. 19, No. 2, pp;229–239, (1976,)–XP000609112.

Perrone et al., "Conformationally restricted thiazole derivatives as novel class of 5-HT3, receptor ligands", IL Farmaco, 50, (2), pp. 77–82, (1995,)–XP000605205.

Yamane K., "Benzocycloheptathiazoles", Chemical Abstract, vol. 73, No. 9, (Aug. 31, 1970)–XP002018029.

Saida et al., "Preparation of thiazoles as tyrosinase inhibitors and skin–lightening preparations containing them", vol. 120, No. 2, (Jan. 10, 1994) –XP002123115.

*Primary Examiner*—Laura L. Stockton
*Attorney, Agent, or Firm*—Foley & Lardner

[57] ABSTRACT

Polycyclic dihydrothiazoles, processes for their preparation, and their pharmaceutical uses are provided. Preferred compounds are represented by the formula I

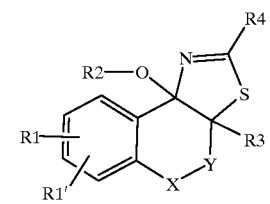

wherein the radicals may have various meanings. The compounds are particularly useful as anorectics.

11 Claims, No Drawings

POLYCYCLIC DIHYDROTHIAZOLES, THEIR PREPARATION, AND USE AS PHARMACEUTICALS

FIELD OF THE INVENTION

The invention relates to polycyclic dihydrothiazoles, and to their physiologically tolerable salts and physiologically functional derivatives.

BACKGROUND OF THE INVENTION

Some thiazolidine derivatives having anorectic action have been described in the art (Austrian Patent No. 365181).

SUMMARY OF THE INVENTION

The invention has the objective of making available further compounds which display a therapeutically utilizable anorectic action. It is one object of the invention to provide compounds that have anorectic action. Another object is to provide a pharmaceutical composition that comprises at least one polycyclic dihydrothiazole. Yet another object of the invention is a process for the production of a pharmaceutical comprising mixing a polycyclic dihydrothiazole with a pharmaceutically suitable vehicle. Other objects of the invention will be apparent from the specification.

Embodiments of the invention relate to compounds, medicants containing such compounds, and processes for preparing medicants, the compounds represented by the formula I

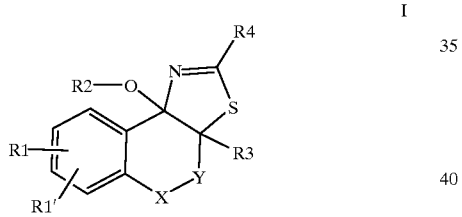

in which

Y is a direct bond, —$CH_2$—, or —$CH_2$—$CH_2$—;

X is $CH_2$, $CH(CH_3)$, $CH(C_2H_5)$, $CH(C_3H_7)$, or $CH(C_6H_5)$;

R1, R' independently of one another are H, F, Cl, Br, I, $CF_3$, $NO_2$, CN, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, and/or O—($C_1$–$C_6$)-alkyl, it being possible in the alkyl radicals for one or more, or all hydrogens to be replaced by F, or a hydrogen to be replaced by OH, OC(O)$CH_3$, OC(O)H, O$CH_2$Ph, $NH_2$, NH—CO—$CH_3$ or N(COO$CH_2$Ph)$_2$; $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl, wherein n can be 0–6 and the phenyl radical can be substituted up to two times by F, Cl, Br, OH, CF3, $NO_2$, CN, $OCF_3$, O—($C_1$–$C_6$)-alkyl, ($C_1$–$C_6$)-alkyl, $NH_2$; $NH_2$, NH—($C_1$–$C_6$)-alkyl, N(($C_1$–$C_6$)-alkyl)$_2$, NH($C_1$–$C_7$)-acyl, phenyl, biphenyl, O—($CH_2$)$_n$-phenyl, wherein n can be 0–6, 1- or 2-naphthyl, 2-, 3- or 4-pyridyl, 2- or 3-furanyl or 2- or 3-thienyl, wherein the phenyl, biphenyl, naphthyl, pyridyl, furanyl or thienyl rings each can be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl, $CONH_2$; 1,2,3-triazol-5-yl, wherein the triazole ring can be substituted in the 1-, 2- or 3-position by methyl or benzyl; tetrazol-5-yl, wherein the tetrazole ring can be substituted in the 1- or 2-position by methyl or benzyl;

R2 is H, ($C_1$–$C_6$)-alkyl, ($C_3$–$C_6$)-cycloalkyl, ($CH_2$)$_{n2}$-phenyl, ($CH_2$)$_{n1}$-thienyl, ($CH_2$)$_{n1}$-pyridyl, ($CH_2$)$_{n1}$-furyl, C(O)—($C_1$–$C_6$)-alkyl, C(O) ($C_3$–$C_6$)-cycloalkyl, C(O)—($CH_2$)$_{n1}$-phenyl, C(O)—($CH_2$)$_{n1}$-thienyl, C(O)—($CH_2$)$_{n1}$-pyridyl, C(O)—($CH_2$)$_{n1}$-furyl, wherein $_{n1}$ can be 0–5 and in which phenyl, thienyl, pyridyl, furyl each can be substituted up to two times by Cl, F, CN, $CF_3$, ($C_1$–$C_3$)-alkyl, OH, O—($C_1$–$C_6$)-alkyl;

R3 is H, ($C_1$–$C_6$)-alkyl, F, CN, $N_3$, O—($C_1$–$C_6$)-alkyl, ($CH_2$)$_{n1}$-phenyl, ($CH_2$)$_{n1}$-thienyl, ($CH_2$)$_{n1}$-pyridyl, ($CH_2$)$_{n1}$-furyl, wherein n1 can be 0–5 and in which phenyl, thienyl, pyridyl, furyl each can be substituted up to two times by Cl, F, CN, $CF_3$, ($C_1$–$C_3$)-alkyl, OH, O—($C_1$–$C_6$)-alkyl; ($C_2$–$C_6$)-alkynyl, ($C_2$–$C_6$)-alkenyl, C(O)O$CH_3$, C(O)O$CH_2CH_3$, C(O)OH, C(O)$NH_2$, C(O)NH$CH_3$, C(O)N($CH_3$)$_2$, OC(O)$CH_3$;

R4 is ($C_1$–$C_8$)-alkyl, ($C_3$–$C_7$)-cycloalkyl, ($C_2$–$C_6$)-alkenyl, ($C_2$–$C_6$)-alkynyl, ($C_4$–$C_7$)-cycloalkenyl, it being possible in the alkyl radicals for one or more, or all hydrogens to be replaced by F or a hydrogen to be replaced by OH, OC(O)$CH_3$, OC(O)H,O—$CH_2$—Ph or O—($C_1$–$C_4$)-alkyl; ($CH_2$)$_{n2}$—NR6R7, wherein n2 can be 1–6 and R6 and R7 independently of one another can be H, ($C_1$–$C_6$)-alkyl, ($C_3$–$C_6$)-cycloalkyl, CO—($C_1$–$C_6$)-alkyl, CHO or CO-phenyl, or —NR6R7 is a ring such as pyrrolidine, piperidine, morpholine, piperazine, N-4-methylpiperazin-1-yl, N-4-benzylpiperazin-1-yl, phthalimidoyl; ($CH_2$)$_n$-aryl, wherein n can be 0–6 and aryl can be phenyl, biphenyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methyl-imidazol-2-, -4- or -5-yl and the aryl radical or heteroaryl radical can be substituted up to two times by F, Cl, Br, OH, $CF_3$, $NO_2$, CN, $OCF_3$, O—($C_1$–$C_6$)-alkyl, S—($C_1$–$C_6$)-alkyl, SO—($C_1$–$C_6$)-alkyl, $SO_2$—($C_1$–$C_6$)-alkyl, ($C_1$–$C_6$)-alkyl, ($C_3$–$C_6$)-cycloalkyl, COOH, COO($C_1$–$C_6$)alkyl, COO($C_3$–$C_6$)-cycloalkyl, $CONH_2$, CONH($C_1$–$C_6$)alkyl, CON[($C_1$–$C_6$)alkyl]2, CONH($C_3$–$C_6$)cycloalkyl, $NH_2$, NH—CO—($C_1$–$C_6$)-alkyl, NH—CO-phenyl, pyrrolidin-1-yl, morpholin-1-yl, piperidin-1-yl, piperazin-1-yl, 4-methylpiperazin-1-yl, ($CH_2$)$_{n3}$-phenyl, O—($CH_2$)$_{n3}$-phenyl, S—($CH_2$)$_n$-phenyl, $SO_2$-($CH_2$)n-phenyl, wherein n3=0–3;

and their physiologically tolerable salts and physiologically functional derivatives.

DETAILED DESCRIPTION OF THE PREFERRED EMBODIMENTS

The inventors discovered that the compounds of the formula I are distinguished by their favorable effects on lipid metabolism; in particular, they are suitable as anorectics/ slimming preparations. The compounds can be employed on their own or in combination with further slimming preparations (such as are described, for example, in Chapter D1 of the Roten Liste). The compounds are suitable for the prophylaxis and in particular for the treatment of obesity. The compounds are furthermore suitable for the prophylaxis and in particular for the treatment of type II diabetes.

a. Preferred Compounds

Preferred compounds of the formula I are those in which one or more radicals has or have the following meaning:

Y is a direct bond;

X is $CH_2$;

R1, R1' independently of one another are H, F, Cl, Br, I, $CF_3$, $NO_2$, CN, COOH, $COO(C_1-C_6)$alkyl, $CONH_2$, $CONH(C_1-C_6)$alkyl, $CON[(C_1-C_6)$alkyl$]_2$, $(C_1-C_6)$-alkyl, $(C_2-C_6)$-alkenyl, $(C_2-C_6)$-alkynyl, $O-(C_1-C_6)$-alkyl, it being possible in the alkyl radicals for one or more, or all hydrogens to be replaced by F, or a hydrogen to be replaced by OH, $OC(O)CH_3$, $OC(O)H$, $O-CH_2-Ph$, $NH_2$, $NH-CO-CH_3$ or $N(COOCH_2Ph)_2$; $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, $SO_2-(CH_2)_n$-phenyl, wherein n can be 0–6 and the phenyl radical can be substituted up to two times by F, Cl, Br, OH, $CF_3$, $NO_2$, CN, $OCF_3$, $O-(C_1-C_6)$-alkyl, $(C1-C_6)$-alkyl, $NH_2$; $NH_2$, $NH-(C_1-C_6)$-alkyl, $N((C_1-C_6)$-alkyl$)_2$, $NH(C_1-C_7)$-acyl, phenyl, biphenyl, $O-(CH_2)_n$-phenyl, wherein n can be 0–6; 1- or 2-naphthyl, 2-, 3- or 4-pyridyl, 2- or 3-furanyl or 2- or 3-thienyl, wherein the phenyl, biphenyl, naphthyl, pyridyl, furanyl or thienyl rings each can be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, $CONH_2$; 1,2,3-triazol-5-yl, wherein the triazole ring can be substituted in the 1-, 2- or 3-position by methyl or benzyl; tetrazol-5-yl, wherein the tetrazole ring can be substituted in the 1- or 2-position by methyl or benzyl;

R2 is H, $(C_1-C_6)$-alkyl, $(C_3-C_6)$-cycloalkyl, $(CH_2)_{n1}$-phenyl, $(CH_2)_{n1}$-thienyl, $(CH_2)_{n1}$-pyridyl, $(CH_2)_{n1}$-furyl, $C(O)-(C_1-C_6)$-alkyl, $C(O)-(C_3-C_6)$-cycloalkyl, $C(O)-(CH_2)_{n1}$-phenyl, $C(O)-(CH_2)_{n1}$-thienyl, $C(O)-(CH_2)_{n1}$-pyridyl, $C(O)-(CH_2)_{n1}$-furyl, wherein n1 can be 0–5 and in which phenyl, thienyl, pyridyl, furyl each can be substituted up to two times by Cl, F, CN, $CF_3$, $(C_1-C_3)$-alkyl, OH, $O-(C_1-C_6)$-alkyl;

R3 is H, $(C_1-C_6)$-alkyl, F, CN, $N_3$, $O-(C_1-C_6)$-alkyl, $(CH_2)_{n1}$-phenyl, $(CH_2)_{n1}$-thienyl, $(CH_2)_{n1}$-pyridyl, $(CH_2)_{n1}$-furyl, wherein n1 can be 0–5 and in which phenyl, thienyl, pyridyl, furyl each can be substituted up to two times by Cl, F, CN, $CF_3$, $(C_1-C_3)$-alkyl, OH, $O-(C_1-C_6)$-alkyl; $(C_2-C_6)$-alkynyl, $(C_2-C_6)$-alkenyl, $C(O)OCH_3$, $C(O)OCH_2CH_3$, $C(O)OH$, $C(O)NH_2$, $C(O)NHCH_3$, $C(O)N(CH_3)_2$, $OC(O)CH_3$;

R4 is $(C_1-C_8)$-alkyl, $(C_3-C_7)$-cycloalkyl, $(C_2-C_6)$-alkenyl, $(C_2-C_6)$-alkynyl, $(C_4-C_7)$-cycloalkenyl, it being possible in the alkyl radicals for one or more, or all hydrogens to be replaced by F or a hydrogen to be replaced by OH, $OC(O)CH_3$, $OC(O)H$, $O-CH_2-Ph$ or $O-(C_1-C_4)$-alkyl; $(CH_2)_{n2}-NR6R7$, wherein n2 can be 1–6 and R6 and R7 independently of one another can be H, $(C_1-C_6)$-alkyl, $(C_3-C_6)$-cycloalkyl, $CO-(C_1-C_6)$-alkyl, CHO or CO-phenyl or $-NR6R7$ is a ring such as pyrrolidine, piperidine, morpholine, piperazine, N-4-methylpiperazin-1-yl, N-4-benzylpiperazin-1-yl, phthalimidoyl; $(CH_2)_n$-aryl, wherein n can be 0–6 and aryl can be phenyl, biphenyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methyl-imidazol-2-, -4- or -5-yl and the aryl radical or heteroaryl radical can be substituted up to two times by F, Cl, Br, OH, $CF_3$, $NO_2$, CN, $OCF_3$, $O-(C_1-C_6)$-alkyl, $S-(C_1-C_6)$-alkyl, $SO-(C_1-C_6)$-alkyl, $SO_2-(C_1-C_6)$-alkyl, $(C_1-C_6)$-alkyl, $(C_3-C_6)$-cycloalkyl, COOH, $COO(C_1-C_6)$alkyl, $COO(C_3-C_6)$cycloalkyl, $CONH_2$, $CONH-(C_1-C_6)$alkyl, $CON[(C_1-C_6)$alkyl$]_2$, $CONH(C_3-C_6)$cycloalkyl, $NH_2$, $NH-CO-(C_1-C_6)$-alkyl, $NH-CO$-phenyl, pyrrolidin-1-yl, morpholin-1-yl, piperidin-1-yl, piperazin-1-yl, 4-methylpiperazin-1-yl, $(CH_2)_{n3}$-phenyl, $O-(CH_2)_{n3}$-phenyl, $S-(CH_2)_{n3}$-phenyl, $SO_2-(CH_2)_{n3}$-phenyl, wherein n3=0–3;

and their physiologically tolerable salts and physiologically functional derivatives.

Particularly preferred compounds of the formula I are those in which one or more radicals has or have the following meaning:

Y is a direct bond;

X is $CH_2$;

R1, R1' independently of one another are H, F, Cl, Br, I, CF3, $NO_2$, CN, COOH, $COO(C_1-C_6)$alkyl, $CONH_2$, $CONH(C_1-C_6)$alkyl, $CON[(C_1-C_6)$alkyl$]_2$, $(C_1-C_6)$-alkyl, $(C_2-C_6)$-alkenyl, $(C_2-C_6)$-alkynyl, and/or $O-(C_1-C_6)$-alkyl, it being possible in the alkyl radicals for one or more, or all hydrogens to be replaced by F, or a hydrogen to be replaced by OH, $OC(O)CH_3$, $OC(O)H$, $O-CH_2-Ph$, $NH_2$, $NH-CO-CH_3$ or $N(COOCH_2Ph)_2$; $SO_2-NH_2$, $SO_2NH(C_1-C_6)$-alkyl, $SO_2N[(C_1-C_6)$-alkyl$]2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, $SO_2-(CH_2)_n$-phenyl, wherein n can be 0–6 and the phenyl radical can be substituted up to two times by F, Cl, Br, OH, $CF_3$, $NO_2$, CN, $OCF_3$, $O-(C_1-C_6)$-alkyl, $(C_1-C_6)$-alkyl, $NH_2$; $NH_2$, $NH-(C_1-C_6)$-alkyl, $N((C_1-C_6)$-alkyl$)_2$, $NH(C_1-C_7)$-acyl, phenyl, biphenyl, $O-(CH_2)$n-phenyl, wherein n can be 0–6, 1- or 2-naphthyl, 2-, 3- or 4-pyridyl, 2- or 3-furanyl or 2- or 3-thienyl, wherein the phenyl, biphenyl, naphthyl, pyridyl, furanyl or thienyl rings each can be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, $CONH_2$; 1,2,3-triazol-5-yl, wherein the triazole ring can be substituted in the 1-, 2- or 3-position by methyl or benzyl; tetrazol-5-yl, wherein the tetrazole ring can be substituted in the 1- or 2-position by methyl or benzyl;

R2 is H, $(C_1-C_6)$-alkyl, $(C_3-C_6)$-cycloalkyl, $(CH_2)_{n1}$-phenyl, $(CH_2)_{n1}$-thienyl, $(CH_2)_{n1}$-pyridyl, $(CH_2)_{n1}$-furyl, $C(O)-(C_1-C_6)$-alkyl, $C(O)-(C_3-C_6)$-cycloalkyl, $C(O)-(CH_2)_{n1}$-phenyl, $C(O)-(CH_2)_{n1}$-thienyl, $C(O)-(CH_2)_{n1}$-pyridyl, $C(O)-(CH_2)_{n1}$-furyl, wherein n1 can be 0–5 and in which phenyl, thienyl, pyridyl, furyl each can be substituted up to two times by Cl, F, CN, $CF_3$, $(C_1-C_3)$-alkyl, OH, $O-(C_1-C_6)$-alkyl;

R3 is H, F;

R4 is $(C_1-C_8)$-alkyl, $(C_3-C_7)$-cycloalkyl, $(C_2-C_6)$-alkenyl, $(C_2-C_6)$-alkynyl, $(C_4-C_7)$-cycloalkenyl, it being possible in the alkyl radicals for one or more, or all hydrogens to be replaced by F or a hydrogen to be replaced by OH, $OC(O)CH_3$, $OC(O)H,O-CH_2-Ph$ or $O-(C_1-C_4)$-alkyl; $(CH_2)_n-NR6R7$, wherein n can be 1–6 and R6 and R7 independently of one another can be H, $(C_1-C_6)$-alkyl, $(C_3-C_6)$-cycloalkyl, $CO-(C_1-C_6)$-alkyl, CHO or CO-phenyl, or —NR6R7 is a ring such as pyrrolidine, piperidine, morpholine, piperazine, N4-methylpiperazin-1-yl, N4-benzylpiperazin-1-yl, phthalimidoyl; $(CH_2)$n-aryl, wherein n can be 0–6 and aryl can be phenyl, biphenyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methyl-imidazol-2-, -4- or -5-yl and the aryl radical or heteroaryl radical can be substituted up to two times by F, Cl, Br, OH, $CF_3$, $NO_2$, CN, $OCF_3$, $O-(C_1-C_6)$-alkyl, $S-(C_1-C_6)$-alkyl, $SO-(C_1-C_6)$-alkyl, $SO_2-(C_1-C_6)$-alkyl, $(C_1-C_6)$-alkyl, $(C_3-C_6)$-cycloalkyl, COOH, $COO(C_1-C_6)$alkyl, $COO(C_3-C_6)$ cycloalkyl, $CONH_2$, $CONH-(C_1-C_6)$alkyl, $CON[(C_1-C_6)alkyl]_2$, $CONH(C_3-C_6)$cycloalkyl, $NH_2$, $NH-CO-(C_1-C_6)$-alkyl, NH—CO-phenyl, pyrrolidin-1-yl, morpholin-1-yl, piperidin-1-yl, piperazin-1-yl, 4-methylpiperazin-1-yl, $(CH_2)_{n3}$-phenyl, $O-(CH_2)_{n3}$-phenyl, $S-(CH_2)_{n3}$-phenyl, $SO_2-(CH_2)_{n3}$-phenyl, wherein n3 =0–3;

and their physiologically tolerable salts.

Very particularly preferred compounds of the formula I are those in which one or more radicals has or have the following meaning:

Y is a direct bond;

X is $CH_2$;

R1, R1' independently of one another are H, F, Cl, Br, $NO_2$, CN, COOH, $(C_1-C_6)$-alkyl, $(C_2-C_6)$-alkenyl, $(C_2-C_6)$-alkynyl, $O-(C_1-C_6)$-alkyl, $OCF_3$, $OCH_2CF_3$, phenyl, and/or $O-(CH_2)_n$-phenyl, wherein n can be 0–6, 1- or 2-naphthyl, 2- or 3-thienyl, wherein the phenyl, naphthyl or thienyl rings each can be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$;

R2 is H, $(C_1-C_6)$-alkyl, $(C_3-C_6)$-cycloalkyl, $(CH_2)_{n1}$-phenyl, wherein n1 can be 0–5;

R3 is H, F;

R4 is $(C_1-C_8)$-alkyl, $(C_3-C_7)$-cycloalkyl, $(CH_2)_{n2}$—NR6R7, wherein $n_2$ can be 1–6 and R6 and R7 independently of one another can be H, $(C_1-C_6)$-alkyl, or —NR6R7 is a ring such as pyrrolidine, piperidine, morpholine, piperazine, N4-methylpiperazin-1-yl, N4-benzylpiperazin-1-yl, phthalimidoyl; $(CH_2)_n$-Aryl, wherein n can be 0–6 and aryl can be phenyl, biphenyl, 1- or 2-naphthyl, 2-, 3- or 4-pyridyl, 2-or3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, -4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methyl-imidazol-2-, -4- or -5-yl and the aryl radical or heteroaryl radical can be substituted up to two times by F, Cl, Br, OH, $CF_3$, $NO_2$, CN, $OCF_3$, $O-(C_1-C_6)$-alkyl, pyrrolidin-1-yl, morpholin-1-yl, piperidin-1-yl, piperazin-1-yl, 4-methylpiperazin-1-yl; and their physiologically tolerable salts.

Furthermore, very particularly preferred compounds of the formula I are those in which one or more radicals has or have the following meaning:

Y is a direct bond;

X is $CH_2$;

R1 is Cl;

R1' is H;

R2 is H;

R3 is H;

R4 is phenyl;

and their physiologically tolerable salts.

The invention relates to compounds of the formula I, to their racemates, racemic mixtures and pure enantiomers, and to their diastereomers and mixtures thereof.

The alkyl, alkenyl and alkynyl radicals in the substituents R1, R1', R2, R3 and R4 can be either straight-chain or branched.

b. Preferred Pharmaceutical Compositions

On account of their higher water solubility, pharmaceutically tolerable salts are particularly suitable for medicinal applications compared with the starting or base compounds. These salts must have a pharmaceutically tolerable anion or cation. Suitable pharmaceutically tolerable acid addition salts of the compounds according to the invention are salts of inorganic acids, such as hydrochloric acid, hydrobromic, phosphoric, metaphosphoric, nitric, sulfonic and sulfuric acid and organic acids, such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acid. For medicinal purposes, the chlorine salt is particularly preferably used. Suitable pharmaceutically tolerable basic salts are ammonium salts, alkali metal salts (such as sodium and potassium salts) and alkaline earth metal salts (such as magnesium and calcium salts).

Salts with a nonpharmaceutically tolerable anion are likewise included in the scope of the invention as useful intermediates for the production or purification of pharmaceutically tolerable salts and/or for use in nontherapeutic, for example in-vitro, applications.

The expression "physiologically functional derivative" used here relates to any physiologically tolerable derivative of a compound of the formula I according to the invention, e.g. an ester, which on administration to a mammal, such as, for example, man, is able (directly or indirectly) to form a compound of the formula I or an active metabolite thereof.

The physiologically functional derivatives also include prodrugs of the compounds according to the invention. Such prodrugs can be metabolized in vivo to a compound according to the invention. These prodrugs can themselves be active or inactive.

The compounds according to the invention can also be present in various polymorphic forms, e.g. as amorphous and crystalline polymorphic forms. All polymorphic forms of the compounds according to the invention are included in the scope of the invention and are a further aspect of the invention.

Below, all references to "compound(s) (according to formula (I)" refer to compound(s) of the formula (I) as described above, and their salts, solvates and physiologically functional derivatives as described herein.

The amount of a compound according to formula (I) which is necessary in order to achieve the desired biological effect is dependent on a number of factors, e.g. the specific compound selected, the intended use, the manner of administration and the clinical condition of the patient. In general, the daily dose is in the range from 0.3 mg to 100 mg (typically from 3 mg to 50 mg) per day per kilogram of body weight, e.g. 3–10 mg/kg/day. An intravenous dose can be, for example, in the range from 0.3 mg to 1.0 mg/kg, which can be suitably administered as an infusion of 10 ng to 100 ng per kilogram per minute. Suitable infusion solutions for these purposes can contain, for example, from 0.1 ng to 10 mg, typically from 1 ng to 10 mg per milliliter. Individual doses can contain, for example, from 1 mg to 10 g of the active compound. Thus, ampoules for injections can contain, for example, from 1.0 to 1000 mg typically from 1 mg to 100 mg, and orally administrable individual dose formulations, such as, for example, tablets or capsules, can contain, for example, from 10 to 600 mg. In the case of pharmaceutically tolerable salts, the abovementioned weight details relate to the weight of the dihydrothiazolium ion derived from the salt. For the prophylaxis or therapy of the abovementioned conditions, the compounds according to formula (I) can be used as the compound itself, but they are preferably present in the form of a pharmaceutical composition with a tolerable vehicle. The vehicle must of course be tolerable, in the sense that it is compatible with the other constituents of the composition and is not harmful to the patient's health. The vehicle can be a solid or a liquid or both and is preferably formulated with the compound as an individual dose, for example as a tablet which can contain from 0.05% to 95% by weight of the active compound. Further pharmaceutically active substances can also be present, including further compounds according to formula (I). The pharmaceutical compositions according to the invention can be prepared by one of the known pharmaceutical methods, which essentially consist in mixing the constituents with pharmacologically tolerable excipients and/or auxiliaries.

c. Administration of the Pharmaceutical Compositions

Pharmaceutical compositions according to the invention are those which are suitable for oral, rectal, topical, peroral (e.g. sublingual) and parenteral (e.g. subcutaneous, intramuscular, intradermal or intravenous) administration, although the most suitable manner of administration in each individual case is dependent on the nature and severity of the condition to be treated and on the nature of the compound according to formula (I) used in each case. Sugar-coated formulations and sugar-coated delayed release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets which in each case contain a certain amount of the compound according to formula (I); as powder or granules; as a solution or suspension in an aqueous or nonaqueous liquid; or as an oil-in-water or water-in-oil emulsion. As already mentioned, these compositions can be prepared by any suitable pharmaceutical method which includes a step in which the active compound and the vehicle (which can consist of one or more additional constituents) are brought into contact. In general, the compositions are prepared by uniform and homogeneous mixing of the active compound with a liquid and/or finely divided solid vehicle, after which the product, if necessary, is shaped. Thus a tablet, for example, can be prepared by pressing or shaping a powder or granules of the compound, if appropriate with one or more additional constituents. Pressed tablets can be prepared by tabletting the compound in free-flowing form, such as, for example, a powder or granules, if appropriate mixed with a binder, lubricant, inert diluent and/or one (a number of) surface-active/dispersing agents in a suitable machine. Shaped tablets can be prepared by shaping the pulverulent compound, moistened with an inert liquid diluent, in a suitable machine.

Pharmaceutical compositions which are suitable for peroral (sublingual) administration include lozenges which contain a compound according to formula (I) with a flavoring, customarily sucrose and gum arabic or tragacanth, and pastilles which include the compound in an inert base such as gelatin and glycerol or sucrose and gum arabic.

Suitable pharmaceutical compositions for parenteral administration preferably include sterile aqueous preparations of a compound according to formula (I), which are preferably isotonic with the blood of the intended recipient. These preparations are preferably administered intravenously although the administration can also take place subcutaneously, intramuscularly or intradermally as an injection. These preparations can preferably be prepared by mixing the compound with water and rendering the obtained solution sterile and isotonic with the blood. Injectable compositions according to the invention in general contain from 0.1 to 5% by weight of the active compound.

Suitable pharmaceutical compositions for rectal administration are preferably present as individual dose suppositories. These can be prepared by mixing a compound according to formula (I) with one or more conventional solid vehicles, for example cocoa butter, and shaping the resulting mixture.

Suitable pharmaceutical compositions for topical application to the skin are preferably present as an ointment, cream, lotion, paste, spray, aerosol or oil. Vehicles which can be used are petroleum jelly, lanolin, polyethylene glycols, alcohols and combinations of two or more of these substances. The active compound is in general present in a concentration of 0.1 to 15% by weight of the composition, for example of 0.5 to 2%.

Transdermal administration is also possible. Suitable pharmaceutical compositions for transdermal administration can be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is about 1% to 35%, preferably about 3% to 15%. As a particular possibility, the active compound can be released by electrotransport or iontophoresis, as described, for example, in Pharmaceutical Research, 2(6): 318 (1986).

d. Processes to Prepare the Compounds

The invention furthermore relates to a process for the preparation of the compounds of the formula I, which comprises obtaining the compounds of the formula I in such a way that the procedure is according to the following reaction scheme:

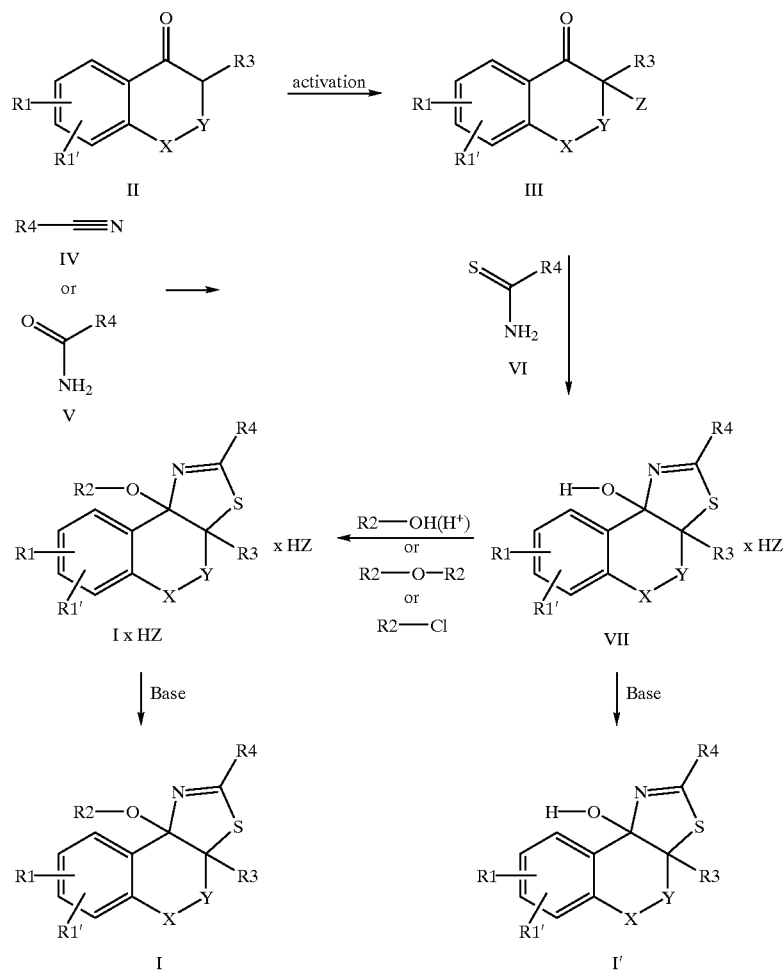

For this, compounds of the formula II

Formula II

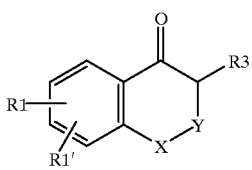

in which R1, R1', R3 and X and Y have the meaning indicated, are activated and converted into a compound of the formula III, in which Z is the radical of an activated ester of an inorganic or organic acid. The compounds of the formula III are reacted further with thioamides of the formula VI

VI

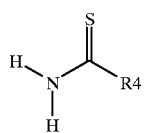

in which R4 has the meaning indicated, to give compounds of the formula VII or I', where, if appropriate, the compounds of the formula I' are converted into their acid addition salts of the formula VII using organic or inorganic acids or salts of the formula VII obtained are converted into the free basic compounds of the formula I' using organic or inorganic bases.

Suitable inorganic acids are, for example: hydrohalic acids such as hydrochloric acid and hydrobromic acid, as well as sulfuric acid, phosphoric acid and amidosulfonic acid.

Organic acids which may be mentioned are, for example: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazine-4(3H)-one-2,2-dioxide.

The procedure described above is advantageously carried out such that the compounds III are reacted with the thioamides VI in the molar ratio from 1:1 to 1:1.5. The reaction is advantageously carried out in an inert solvent, e.g. in polar organic solvents such as dimethylformamide, dimethylacetamide, N-methyl-2-pyrrolidone, dioxane, tetrahydrofuran, acetonitrile, nitromethane or diethylene glycol dimethyl ether. Particularly advantageous solvents, however, have proved to be methyl acetate and ethyl acetate, short-chain alcohols such as methanol, ethanol, propanol, isopropanol, and lower dialkyl ketones, such as, for example, acetone, butane-2-one or hexane-2-one. Mixtures of the reaction media mentioned can also be used; and mixtures of the solvents mentioned can also be used with solvents which taken per se are less suitable, such as, for example, mixtures of methanol with benzene, ethanol with toluene, methanol with diethyl ether or with tert-butyl methyl ether, ethanol with tetrachloromethane, acetone with chloroform, dichloromethane or 1,2-dichloroethane, wherein the more polar solvent in each case should expediently be used in an excess. The reaction components can be suspended or dissolved in the respective reaction medium. Fundamentally, the reaction components can also be reacted without solvent, in particular if the respective thioamide has a melting point which is as low as possible. The reaction proceeds in an only slightly exothermic manner and can be carried out between −10° C. and 150° C., preferably between 30° C. and 100° C. A temperature range between 50° C. and 90° C. as a rule proves to be particularly favorable.

The reaction time is largely dependent on the reaction temperature and is between 2 minutes and 3 days at relatively high and relatively low temperatures respectively. In the favorable temperature range, the reaction time is in general between 5 minutes and 48 hours.

Frequently, the compounds VII separate in the form of their poorly soluble acid addition salts in the course of the reaction, expediently a suitable precipitating agent is additionally subsequently added. Those used are, for example, hydrocarbons such as benzene, toluene, cyclohexane or heptane or tetrachloromethane; in particular, alkyl acetates such as ethyl acetate or n-butyl acetate or dialkyl ethers such as diethyl ether, diisopropyl ether, di-n-butyl ether or tert-butyl methyl ether prove particularly suitable. If the reaction mixture remains in solution after the end of the reaction, the salts of the compounds VII can be precipitated using one of the precipitating agents mentioned, if appropriate after concentration of the reaction solution. Furthermore, the solution of the reaction mixture can also be advantageously filtered into the solution of one of the precipitating agents mentioned with stirring. Since the reaction of the compounds III with the thioamides V proceeds virtually quantitatively, the crude products obtained are usually already analytically pure. The working-up of the reaction mixture can also be carried out such that the reaction mixture is rendered alkaline with addition of an organic base, such as, for example, triethylamine or diisobutylamine or ammonia or morpholine or piperidine or 1,8-diazabicyclo[5.4.0]undec-7-ene, and the crude reaction product is purified chromatographically, e.g. on a silica gel column, after concentration. Suitable elution media for this prove to be, for example, mixtures of ethyl acetate with methanol, mixtures of dichloromethane with methanol, mixtures of toluene with methanol or ethyl acetate or mixtures of ethyl acetate with hydrocarbons such as heptane. If the purification of the crude product is carried out in the manner last described, an acid addition product of the formula VII can be obtained from the pure base of the formula I' thus obtained by dissolving or suspending the base in an organic protic solvent such as methanol, ethanol, propanol or isopropanol or in an organic aprotic solvent such as ethyl acetate, diethyl ether, diisopropyl ether, tert-butyl methyl ether, dioxane, tetrahydrofuran, acetone or butan-2-one and then treating this mixture with an at least equimolar amount of an inorganic acid such as, for example, hydrochloric acid, dissolved in an inert solvent such as, for example, diethyl ether or ethanol, or another of the inorganic or organic acids mentioned further above.

The compounds of the formula I' can be recrystallized from an inert, suitable solvent such as, for example, acetone, butan-2-one, acetonitrile, nitromethane. Particularly advantageous, however, is reprecipitation from a solvent such as, for example, dimethylformamide, dimethylacetamide, nitromethane, acetonitrile, preferably methanol or ethanol.

The reaction of the compounds of the formula II with the thioamides of the formula VI can also be carried out such that an at least equimolar amount of a base, such as, for example, triethylamine, is added to the reaction mixture and the compounds I' thus obtained are then optionally converted into their acid addition products VII.

A possible radical of an activated ester Z in the compounds of the formula III is, for example: Cl, Br, I, O—C(O)—($C_6H_4$)-4-$NO_2$, O—$SO_2$—$CH_3$, O—$SO_2$—$CF_3$, O—$SO_2$—($C_6H_4$)-4-$CH_3$, O—$SO_2$—$C_6H_4$.

The acid addition products VII and I×HZ can be reacted to give the compounds of the formulae I and I' by treatment with bases. Possible bases are, for example, solutions of inorganic hydroxides, such as lithium, sodium, potassium, calcium or barium hydroxide, carbonates or hydrogencarbonates, such as sodium or potassium carbonate, sodium or potassium hydrogencarbonate, ammonia and amines, such as triethylamine, diisopropylamine, dicyclohexylamine, piperidine, morpholine, methyldicyclohexylamine.

Thioamides of the formula VI are either commercially obtainable or can be obtained, for example, by reaction of the corresponding carboxamide V with phosphorus pentasulfide in pyridine (R. N. Hurd, G. Delameter, Chem. Rev. 61, 45 (1961)), or with Lawesson's reagent in toluene, pyridine, hexamethylphosphoramide [Scheibye, Pedersen und Lawesson: Bull. Soc. Chim. Belges 87, 229 (1978)], preferably in a mixture of tetrahydrofuran with 1,3-dimethyl-3,4,5,6-tetrahydro-2(1H)-pyrimidinone or 1,3-dimethyl-2-imidazolidinone. Hydroxyl, amino or additional carbonyl functions are in this case expediently protected using a removable protective function, such as, for example, a benzyl, tert-butyloxycarbonyl or benzyloxycarbonyl radical or converted into an optionally cyclic acetal. Methods for this are described, for example, in Th. W. Greene and P. G. M. Wuts, Protective Groups in Organic Synthesis, Second Edition, 1991, John Wiley & Sons, New York.

Thioamides of the formula VI are also obtainable by reacting nitriles of the formula IV

Formula IV with hydrogen sulfide (Houben-Weyl IX, 762) or thioacetamide (E. C. Taylor, J. A. Zoltewicz, J. Am. Chem. Soc. 82, 2656 (1960)) or O,O-diethyl-dithiophosphoric acid. The reactions with hydrogen sulfide are preferably carried out in an organic solvent such as methanol or ethanol, those with thioacetamide in a solvent such as dimethylformamide with addition of hydrochloric acid, and those with O,O-diethyidithiophosphoric acid in a solvent such as ethyl acetate under acidic, e.g. HCl, conditions at room temperature or with warming.

The compounds of the formula I×HZ or I, wherein R2 is ($C_1$–$C_6$)-alkyl, ($C_3$–$C_6$)-cycloalkyl, $(CH_2)_n$-phenyl, $(CH_2)_n$-thienyl, $(CH_2)_n$-pyridyl, $(CH_2)_n$-furyl, and wherein n can be 0–5, can be obtained by either aa) allowing the acid addition salts of the formula VII to react in a solvent of the formula R2—OH, wherein R2 has the meaning described above, at a temperature from −20° C. to 120° C., preferably at −5° C. to 50° C., for 2 hours to 4 days, preferably 4 hours to 2 days, or ab) reacting the free bases of the formula I' in a solvent of the formula R2—OH, wherein R2 has the meaning described above, using equimolar, substoichiometric or catalytic, preferably catalytic, amounts of an inorganic or organic acid, such as are described further above, or with addition of an acidic ion exchanger at a temperature of −20° C. to 120° C., preferably at −5° C. to 50° C., for 2 hours to 4 days, preferably 4 hours to 2 days, or ac) carrying out the reactions as in aa) and ab) in an inert aprotic solvent such as dichloromethane, chloroform, 1,2-dichloroethane, heptane, benzene, toluene, acetonitrile, nitromethane, dioxane, tetrahydrofuran, ethylene glycol dimethyl ether, diethyl ether, diisopropyl ether, tert-butyl methyl ether, acetone, butan-2-one or lower alkyl acetates, such as, for example, ethyl acetate, by addition of 1 to 5, preferably 1.5–2, equivalents of a compound of the formula R2—OH or ad) converting compounds of the formula I' into their alkoxide in a polar aprotic solvent, such as, for example, tetrahydrofuran, dioxane, ethylene glycol dimethyl ether, nitromethane, acetonitrile or dimethylformamide, dimethylacetamide or N-methyl-2-pyrrolidone, with the aid of a base, such as, for example, sodium hydride, lithium diisopropylamide, KOH or potassium carbonate, and then allowing this to react with addition of an alkylating agent of the formula R2—W, wherein W=chlorine, bromine, iodine, O—C(O)—CH$_3$, O—C(O)—CF$_3$, O—C(O)—C$_6$H$_4$-4-NO$_2$, O—SO$_2$—CH$_3$, O—SO$_2$—CF$_3$, O—SO$_2$—C$_6$H$_4$-4-CH$_3$, O—SO$_2$—C$_6$H$_4$-4-NO$_2$, at −20 to 150° C., preferably at −15 to 50° C., for 10 minutes to 2 days, preferably for 20 minutes to 12 hours. Compounds of the formula I×HZ or I wherein R2=C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl, C(O)—(CH$_2$)$_n$-furyl, wherein n can be 0–5, can be obtained by either ba) proceeding as described under aa)–ac), with the difference that instead of an alcohol R2—OH an acid R2—OH is employed, and 1 to 2 equivalents of the acid R2—OH, preferably 1.5 equivalents of the acid R2—OH, are employed and the addition of the acidic inorganic or organic catalyst described under aa)–ac) is dispensed with, but the acidic cation exchanger is advantageously employed or bb) reacting a compound of the formula VII or I' with an acid of the formula R2—OH in the sense of a Mitsunobu reaction (O. Mitsunobu, Synthesis 1981, 1) to give a compound of the formula I×HZ or I or bc) reacting a carbonyl chloride of the formula R2—Cl or a carboxylic anhydride of the formula R2—O—R2 with a compound of the formula I' in the sense of an esterification of an alcohol (Houben-Weyl, Methoden der Organischen Chemie [Methods of Organic Chemistry], Georg Thieme Verlag Stuttgart, Volume E5, pp. 656–715).

All of the publications and patent applications referenced herein are specifically incorporated in their entireties by reference. German patent application 19844547.4 filed Sep. 29, 1998 is specifically incorporated in its entirety by reference.

The following examples are provided to illustrate embodiments of the invention and are not intended to limit the specification or scope of the claims in any way.

EXAMPLES 1 TO 24

Ninetytwo compounds were prepared as summarized in Table 1. Details for the preparation of selected compounds is described further in Examples 1 to 24 below. The other compounds shown in formula I and listed in Table 1 were obtained analogously. The measured melting or decomposition points (m.p.) shown in Table 1 were not corrected and are generally dependent on the heating rate.

Example 1 (Compound A08)

2-Methyl-6-(3-trifluoromethylphenyl)-8,8a-dihydroindeno[1,2-d]thiazol-3a-ol hydrobromide a) 5-(3-Trifluoromethylphenyl)indan-1-one:

1.5 g of 5-bromoindan-1-one, 1.35 g of 3-(trifluoromethyl)phenylboronic acid and 1.5 g of sodium carbonate are suspended with stirring in a mixture of 50 ml of toluene with 10 ml of ethanol and 10 ml of water. Under a protective gas atmosphere (argon), 80 mg of palladium (II)acetate and 186 mg of triphenylphosphine are added and the mixture is stirred for 3 hours under reflux. The ethanol is removed from the cooled reaction mixture by distillation in vacuo, and the residue is treated with 20 ml of 0.5 N sodium hydroxide solution, stirred and filtered. The organic phase of the filtrate is washed a number of times with 20 ml of water in each case and finally with 20 ml of satd sodium chloride solution, dried over magnesium sulfate and concentrated. The residue is chromatographed on silica gel using n-heptane/ethyl acetate 3/1 and 5-(3-trifluoromethylphenyl)indan-1-one of melting point 93° C. is obtained.

b) 2-Bromo-5-(3-trifluoromethylphenyl)indan-1-one:

1.79 g of 5-(3-trifluoromethylphenyl)indan-1-one are dissolved in 10 ml of glacial acetic acid. 5.5 µl of a 48% strength solution of hydrobromic acid in water are added and a solution of 0.362 ml of bromine in 5 ml of glacial acetic acid is then slowly added dropwise. The reaction mixture is stirred at room temperature for 3 hours and then poured into a mixture of 50 ml of water with 50 g of ice and 86 mg of sodium hydrogencarbonate. The aqueous suspension is extracted by shaking with 100 ml of dichloromethane, the organic phase is washed three times with 50 ml of water, dried over magnesium sulfate and concentrated, and the residue is chromatographed on silica gel using toluene/ethyl acetate 25/1. 2-Bromo-5-(3-trifluoromethylphenyl)indan-1-one of melting point 96° C. is obtained. 2,2-Dibromo-5-(3-trifluoromethylphenyl)indan-1-one of melting point 210° C. (dec.) is isolated as a by-product.

c) 2-Methyl-6-(3-trifluoromethylphenyl)-8,8a-dihydroindeno[1,2-d]thiazol-3a-ol hydrobromide:

213 mg of 2-bromo-5-(3-trifluoromethylphenyl)indan-1-one and 48.8 mg of thioacetamide are dissolved in 10 ml of dry acetone and the solution is stirred at 0° C. for 8 h. The precipitate is filtered off with suction, washed with acetone and dried in a high vacuum. 2-Methyl-6-(3-trifluoromethylphenyl)-8,8a-dihydroindeno[1,2-d]thiazol-3a-ol hydrobromide of melting point 245–250° C. (dec.) is obtained.

Example 2 (Compound A14)

6-(3,5-Bistrifluoromethylphenyl)-2-methyl-8,8a-dihydroindeno[1,2-d]thiazol-3a-ol hydrobromide a) 5-(3,5-Bistrifluoromethylphenyl)indan-1-one:

This compound is prepared analogously to the process described in Example 1a using 3,5-(bistrifluoromethyl)phenylboronic acid; melting point: 121° C.

b) 5-(3,5-Bistrifluoromethylphenyl)-2-bromo-indan-1-one:

This compound is prepared analogously to the process described in Example 1b using compound 2a; melting point: 105° C.

c) 6-(3,5-Bistrifluoromethylphenyl)-2-methyl-8,8a-dihydroindeno[1,2-d]-thiazol-3a-ol hydrobromide:

This compound is prepared analogously to the process described in Example 1c using the compound 2b; melting point: 261–264° C. (dec.).

Example 3 (Compound A16)

2-Methyl-6-(3-trifluoromethoxyphenyl)-8,8a-dihydroindeno[1,2-d]thiazol-3a-ol hydrobromide a) 4,4,5,5-Tetramethyl-2-(3-trifluoromethoxyphenyl)-[1,3,2]dioxaborolane:

2.41 g of 3-(trifluoromethoxy)brombenzene are dissolved in 25 ml of diethyl ether and added dropwise to a suspension of 0.28 g of magnesium in 25 ml of diethyl ether such that the solution remains at the boil. After addition is complete, the mixture is stirred under reflux for 2 h. The cooled solution is added dropwise to a solution of 1.16 ml of trimethyl borate in 25 ml of diethyl ether at a temperature of <–50° C. and then stirred at room temperature for 2 h. 5 ml of 40% strength sulfuric acid and 1.21 g of pinacol are successively added to this solution. After 30 minutes, the solvent is removed on a Rotavapor, the residue is neutralized using saturated sodium hydrogencarbonate solution and the mixture is extracted three times with methyl tert-butyl ether. The organic phase is dried over magnesium sulfate and concentrated in vacuo. 4,4,5,5-Tetramethyl-2-(3-trifluoromethoxy-phenyl)-[1,3,2]dioxaborolane is obtained, which is reacted further without further purification.

b) 5-(3-Trifluoromethoxyphenyl)indan-1-one:

This compound is prepared analogously to the process described in Example 1a using 4,4,5,5-tetramethyl-2-(3-trifluoromethoxyphenyl)-[1,3,2]-dioxaborolane; yellowish oil.

c) 2-Bromo-4-trifluoromethoxy-indan-1-one:

This compound is prepared analogously to the process described in Example 1b using the compound 3b; melting point: 64° C. 2,2-dibromo-4-trifluoromethoxyindan-1-one (yellowish oil) is isolated as a by-product.

d) 2-Methyl-6-(3-trifluoromethoxyphenyl)-8,8a-dihydroindeno[1,2-d]thiazol-3a-ol hydrobromide:

This compound is prepared analogously to the process described in Example 1c using compound 3c; melting point: 210–214° C. (dec.).

Example 4 (Compound A22)

2-Methyl-7-(4-trifluoromethylphenyl)-8,8a-dihydro-indeno[1,2-d]thiazol-3a-ol hydrobromide a) 4-(4-Trifluoromethylphenyl)indan-1-one:

This compound is prepared analogously to the process described in Example 1a using 4-bromo-indan-1-one and 4-(trifluoromethyl)phenylboronic acid; melting point: 75–78° C.

b) 2-Bromo-4-(4-trifluoromethylphenyl)indan-1-one:

This compound is prepared analogously to the process described in Example 1b using compound 4a; melting point: 102–105° C. A little of the corresponding dibromo compound is obtained as a by-product.

c) 2-Methyl-7-(4-trifluoromethylphenyl)-8,8a-dihydroindeno[1,2-d]-thiazol-3a-ol hydrobromide:

This compound is prepared analogously to the process described in Example 1c using compound 4b; melting point: 212–215° C. (dec.).

Example 5 (Compound A23)

2-Methyl-5-(4-trifluoromethylphenyl)-8,8a-dihydroindeno[1,2-d]th iazol-3a-ol hydrobromide a) 6-(4-Trifluoromethylphenyl)indan-1-one:

This compound is prepared analogously to the procedure described in Example 1a using 6-bromoindan-1-one and 4-(trifluoromethyl)phenylboronic acid and reacted further without further purification.

b) 2-Bromo-6-(4-trifluoromethylphenyl)indan-1-one:

This compound is prepared analogously to the process described in Example 1b using compound 5a; melting point: 104° C. A little of the corresponding dibromo compound is obtained as a by-product (m.p.: 135° C.).

c) 2-Methyl-5-(4-trifluoromethylphenyl)-8,8a-dihydroindeno[1,2-d]thiazol-3a-ol hydrobromide:

This compound is prepared analogously to the process described in Example 1c using compound 5b; melting point: 220–223° C. (dec.).

Example 6 (Compound A25)

6-Chloro-3a-ethoxy-2-pyridin-3-yl-8,8a-dihydro-3aH-indeno[1,2-d]thiazole a) 2-Bromo-5-chloroindan-1-one:

This compound is prepared analogously to the process described in Example 1b using 5-chloroindan-1-one; melting point: 94–96° C. A little of the corresponding dibromo compound is obtained as a by-product.

b) 6-Chloro-3a-ethoxy-2-pyridin-3-yl-8,8a-dihydro-3aH-indeno[1,2-d]-thiazole:

1 g of 2-bromo-5-chloroindan-1-one and 622 mg of thionicotinamide are suspended in 10 ml of dry ethanol, and the mixture is stirred at room temperature for 2 h and at 70° C. for 8 h. The reaction mixture is cooled, and the precipitate is filtered off with suction, washed with ethanol, stirred with a little water, again filtered off with suction and dissolved in 50 ml of ethyl acetate. This solution is rendered alkaline with triethylamine, treated with 30 ml of water and the organic phase is separated off, washed with water, dried over magnesium sulfate and concentrated in vacuo, and finally the residue is chromatographed on silica gel using ethyl acetate/n-heptane 1/1. 6-Chloro-3a-ethoxy-2-pyridin-3-yl-8,8a-dihydro-3aH-indeno[1,2-d]thiazole of melting point 89–90° C. is obtained.

Example 7 (Compound A75)

6-Chloro-2-pyridin-3-yl-8,8a-dihydroindeno[1,2-d]thiazol-3a-ol of melting point 134–135° C. is obtained in addition to 6-chloro-3a-ethoxy-2-pyridin-3-yl-8,8a-dihydro-3aH-indeno[1,2-d]thiazole on chromatography of Example 6b

Example 8 (Compound A26)

6-Chloro-2-phenyl-8,8a-dihydro-indeno[1,2-d]thiazol-3a-ol

This compound is prepared analogously to the process described in Example 6b using 2-bromo-5-chloroindan-1-one and thiobenzamide; melting point: 155° C.

Example 9 (Compound A33)

6-Chloro-2-phenyl-8,8a-dihydroindeno[1,2-d]-thiazol-3a-ol hydrochloride a) 6-Chloro-2-phenyl-8,8a-dihydroindeno[1,2-d]thiazol-3a-ol hydrobromide:

This compound is prepared analogously to the process described in Example 1c using 2-bromo-5-chloroindan-1-one and thiobenzamide; melting point: 245° C.

b) 6-Chloro-2-phenyl-8,8a-dihydroindeno[1,2-d]thiazol-3a-ol:

A suspension of the compound from Example 9a in ethyl acetate is treated with a saturated aqueous sodium hydrogencarbonate solution and stirred. The organic phase is separated off, washed twice with satd sodium hydrogencarbonate solution, dried over magnesium sulfate and concentrated in vacuo, and the residue is dried in high vacuum. 9b of melting point 155° C. is obtained.

c) 6-Chloro-2-phenyl-8,8a-dihydro-indeno[1,2-d]thiazol-3a-ol hydrochloride:

9 g of the compound from 9b are suspended in 500 ml of ethyl acetate and treated with an excess of ethereal HCl solution in portions with stirring at ice-bath temperature. The mixture is stirred for 1 h at ice-bath temperature, and the precipitate is filtered off with suction, washed with diethyl ether and dried in high vacuum. 9c of melting point 196–199° C. is obtained.

Example 10 (Compound A27)

6-Chloro-3a-methoxy-2-methyl-8,8a-dihydro-3aH-indeno[1,2-d]thiazole a) 6-Chloro-2-methyl-8,8a-dihydroindeno[1,2-d]thiazol-3a-ol hydrochloride:

This compound is prepared analogously to the process described in Examples 9a–c using 2-bromo-5-chloroindan-1-one and thioacetamide; melting point: 183° C.

b) 2 g of the compound of Example 10a are introduced into 50 ml of methanol and the mixture is stirred at room temperature for 2 days. The reaction mixture is concentrated and the residue is partitioned between 200 ml of ethyl acetate and 200 ml of satd sodium hydrogencarbonate solution. The organic phase is separated off, dried over sodium sulfate and concentrated, and the residue is chromatographed on silica gel using ethyl acetate/n-heptane 1/5. 6-Chloro-3a-methoxy-2-methyl-8,8a-dihydro-3aH-indeno[1,2-d]thiazole is obtained as a waxy solid. $^1$H NMR (d$_6$-dmso, 200 MHz) δ [ppm]=7.38 (m, 3H), 4.6 (m, 1H), 3.6 (m, 1H), 3.22 (s, 3H), 3.02 (m, 1H), 2.2 (s, 3H); MS: MH$^+$=254.

Example 11 (Compound A30)

6-Chloro-2-(3-chlorophenyl)-8,8a-dihydroindeno[1,2-d]thiazol-3a-ol hydrobromide

This compound is prepared analogously to the process described in Example 1c using 2-bromo-5-chloroindan-1-one and 3-chlorothiobenzamide; melting point: 205–210° C. (dec.).

Example 12 (Compound A31)

6-Chloro-2-(2,4-dichlorophenyl)-8,8a-dihydroindeno[1,2-d]thiazol-3a-ol hydrobromide This compound is prepared analogously to the process described in Example 1c using 2-bromo-5-chloroindan-1-one and 2,4-dichlorothiobenzamide; melting point: 220–230° C. (dec.).

Example 13 (Compound A37)

6-Chloro-2-ethyl-8,8a-dihydroindeno[1,2-d]thiazol-3a-ol hydrobromide

This compound is prepared analogously to the process described in Example 1c using 2-bromo-5-chloroindan-1-one and thiopropionamide; melting point: 230–240° C. (dec.).

Example 14 (Compound A38)

6-Chloro-2-pyridin-4-yl-8,8a-dihydroindeno[1,2-d]thiazol-3a-ol 0.98 g of 2-bromo-5-chloroindan-1-one and 0.55 g of thioisonicotinamide are dissolved in 40 ml of dry acetone at room temperature and treated with 0.55 ml of triethylamine. The mixture is stirred at room temperature for 2 days. The reaction mixture is concentrated, and the residue is taken up with ethyl acetate and washed twice with water and then twice with satd sodium chloride solution. The organic phase is dried over magnesium sulfate, filtered and concentrated, and the residue is chromatographed on silica gel using ethyl acetate/n-heptane 10/1. 6-Chloro-2-pyridin-4-yl-8,8a-dihydro-indeno[1,2-d]thiazol-3a-ol of melting point 155–160° C. (dec.) is obtained.

Example 15 (Compound A39)

2-Methyl-5-(4-trifluoromethylphenyl)-8,8a-dihydroindeno[1,2-d]thiazol-3a-ol

A suspension of the compound from Example 5c in ethyl acetate is treated with a saturated aqueous sodium hydrogencarbonate solution and stirred. The organic phase is separated off, washed twice with satd sodium hydrogencarbonate solution, dried over magnesium sulfate and concentrated in vacuo, and the residue is dried in a high vacuum. 15 of melting point 213–217° C. is obtained.

Example 16 (Compound A40)

6-Chloro-2-cyclohexyl-8,8a-dihydroindeno[1,2-d]thiazol-3a-ol hydrobromide

This compound is prepared analogously to the process described in Example 1c using 2-bromo-5-chloroindan-1-one and cyclohexanethiocarboxamide; melting point: 170–175° C. (dec.).

Example 17 (Compound A40)

6-Ethynyl-2-phenyl-8,8a-dihydroindeno[1,2-d]thiazol-3a-ol hydrobromide a) 5-Ethynylindan-1-one:

2.11 g of 5-bromoindan-1-one are suspended in 10 ml of degassed triethylamine with 67.2 mg of palladium(II) acetate and 78.6 mg of triphenylphosphine with 2.12 ml of ethynyltrimethylsilane and the mixture is stirred under reflux for 1 h. The cooled reaction mixture is concentrated, taken up with 20 ml of satd sodium hydrogencarbonate solution and 40 ml of ethyl acetate and the organic phase is washed first with water, then with satd sodium chloride solution. The organic phase is dried over magnesium sulfate, filtered and concentrated in vacuo, and the residue is chromatographed on silica gel using n-heptane/ethyl acetate 3/1. 5-Trimethylsilanylethynylindan-1-one is obtained, which is dissolved in 25 ml of methanol and stirred at room temperature for 2 h with potassium carbonate. The reaction mixture is concentrated in vacuo; the residue is stirred with 25 ml of satd sodium hydrogencarbonate solution and 50 ml of ethyl acetate, and the organic phase is then separated off and filtered through a clarifying layer. The filtrate is dried over magnesium sulfate and concentrated in vacuo, and the residue is stirred with n-heptane. The precipitate is filtered off with suction and dried in vacuo. 5-Ethynylindan-1-one of melting point 157° C. is obtained.

b) 2-Bromo-5-ethynylindan-1-one:

This compound is prepared analogously to the process described in Example 1b using compound 17a; melting point: 144° C.

c) 6-Ethynyl-2-phenyl-8,8a-dihydroindeno[1,2-d]thiazol-3a-ol hydrobromide:

This compound is prepared analogously to the process described in Example 1c using 2-bromo-5-ethynylindan-1-one and thiobenzamide; melting point: 133–134° C. (dec.).

Example 18 (Compound A45)

6-Chloro-2-(4-chlorophenyl)-8,8a-dihydroindeno[1,2-d]thiazol-3a-ol

This compound is obtained analogously to the procedure in Example 14 using 2-bromo-5-chloroindan-1-one and 4-chlorothiobenzamide; melting point: 140–144° C.

Example 19 (Compound A48)

2-Phenyl-6-(2,2,2-trifluoroethoxy)-8,8a-dihydroindeno[1,2-d]thiazol-3a-ol hydrobromide a) 5-(2,2,2-Trifluoroethoxy)indan-1-one:

2.2 ml of 2,2,2-trifluoroethanol are added to a stirred mixture of 3.5 g of 5-fluoroindanone, 20 ml of anhydrous dimethylformamide and 4.1 g of anhydrous and ground potassium carbonate and the mixture is stirred at 80° C. for 10 hours. The solvent is removed by distillation under reduced pressure, the residue is dissolved in ethyl acetate and the organic phase is washed a number of times with water. The indanone derivative is obtained as a brownish crystalline solid after chromatography on silica gel using a mixture of equal parts of ethyl acetate and toluene as an eluent. Melting point 93–97° C.

b) 2-Bromo-5-(2,2,2-trifluoroethoxy)indan-1-one:

This compound is obtained by reaction of 0.9 g of 5-(2,2,2-trifluoroethoxy)indan-1-one with 0.2 ml of bromine in 25 ml of ethyl acetate. The compound is used further without further purification.

c) 2-Phenyl-6-(2,2,2-trifluoroethoxy)-8,8a-dihydroindeno[1,2-d]thiazol-3a-ol hydrobromide:

This compound is prepared analogously to the process described in Example 1c using 2-bromo-5-(2,2,2-trifluoroethoxy)indan-1-one and thiobenzamide; melting point: 240–246° C.

Example 20 (Compound A49)

6-(4-Chlorophenoxy)-2-methyl-8,8a-dihydro-indeno[1,2-d]thiazol-3a-ol hydrobromide a) 5-(4-Chlorophenoxy)indan-1-one:

2.82 g of 4-chlorophenol are stirred at room temperature for ½ an hour, after dissolution in 60 ml of anhydrous dimethylacetamide, with 8.2 g of anhydrous and ground potassium carbonate. After addition of 1.5 g of 5-fluoroindanone, the mixture is stirred at 120–130° C. for 10 hours and, after cooling, the solvent is removed by distillation under reduced pressure. The residue is treated with water and extracted a number of times with ethyl acetate. The organic phase is washed with 2N NaOH and subsequently with water, then stirred for 15 minutes after addition of active carbon and the solvent is removed by distillation under reduced pressure after drying over anhydrous magnesium sulfate. The partially crystalline dark residue is purified by column chromatography on silica gel using an eluent consisting of equal parts of ethyl acetate and toluene. Brown crystals, melting point 75–80° C.

2-Bromo-5-(4-chlorophenoxy)indan-1-one

Approximately ½ ml of a solution of 0.25 ml of bromine in 5 ml of glacial acetic acid is added dropwise to a solution of 1.3 g of 5-(4-chlorophenoxy)indan-1-one in 30 ml of glacial acetic acid and the mixture is warmed slowly until the bromine is decolorized and until the evolution of HBr begins. It is then cooled and the remaining quantity of bromine is added dropwise at room temperature, the mixture is stirred for a further 2 hours and the solvent is removed by distillation under reduced pressure. The residual dark oil is used without further purification.

b) 6-(4-Chlorophenoxy)-2-methyl-8,8a-dihydroindeno[1,2-d]thiazol-3a-ol hydrobromide:

This compound is prepared analogously to the process described in Example 1c using 2-bromo-5-(4-chlorophenoxy)indan-1-one and thioacetamide; melting point: 225–228° C.

Example 21 (Compound A62)

3a-Hydroxy-2-pyridin-4-yl-8,8a-dihydro-3aH-indeno[1,2-d]thiazole-6-carbonitrile a) 1-Oxoindan-5-carbonitrile:

9.5 g of 5-bromoindan-1-one and 4.93 g of CuCN are suspended in 10 ml of dimethylformamide and the mixture is refluxed for 4 hours. A solution of 18 g of iron(III) chloride in 5 ml of conc. hydrochloric acid with 30 ml of water is added dropwise with stirring to the cooled, dark-brown, viscous suspension and the mixture is then stirred at 70° C. for 30 minutes. The reaction mixture is extracted three times by shaking with 50 ml of toluene, and the combined organic phases are extracted by shaking with 50 ml of 2N hydrochloric acid and 50 ml of 2N sodium hydroxide solution and then washed with water until neutral. The toluene extract is dried over magnesium sulfate and concentrated in vacuo, and the residue is recrystallized from n-heptane. 1-Oxoindan-5-carbonitrile of melting point 123–125° C. is obtained.

b) 2-Bromo-1-oxoindan-5-carbonitrile:

The bromination of 1-oxoindan-5-carbonitrile is carried out as described in Example 1b and yields 2-bromo-1-oxoindan-5-carbonitrile of melting point 115–118° C.

c) 3a-Hydroxy-2-pyridin-4-yl-8,8a-dihydro-3aH-indeno[1,2-d]thiazole-6-carbonitrile:

This compound is obtained analogously to the procedure in Example 14 using 2-bromo-1-oxoindan-5-carbonitrile and thioisonicotinamide; melting point: 140° C. (dec.).

Example 22 (Compound A67)

2-Ethyl-5-(4-trifluoromethylphenyl)-8,8a-dihydroindeno[1,2-d]thiazol-3a-ol 355 mg (1 mmol) of the compound from Example 5b are dissolved in 5 ml of dry acetone with 2 mmol of thiopropionamide and the mixture is stirred at room temperature for 24 h. The reaction mixture is then stirred further at ice-bath temperature for 2 h, the precipitate is filtered off with suction and suspended in 20 ml of ethyl acetate, and the mixture is treated with 1.5 mmol of triethylamine and stirred at room temperature for 30 minutes. 10 ml of water are added, the mixture is stirred, and the organic phase is separated off, dried over magnesium sulfate and concentrated in vacuo. 2-Ethyl-5-(4-trifluoromethylphenyl)-8,8a-dihydroindeno[1,2-d]thiazol-3a-ol of melting point 145° C. is obtained.

Example 23 (Compound A70)

6-Ethynyl-2-phenyl-8,8a-dihydroindeno[1,2-d]thiazol-3a-ol

The compound from Example 17c is suspended in ethyl acetate, the mixture is neutralized with triethylamine, and the ethyl acetate phase is washed with water, then dried over magnesium sulfate and concentrated in vacuo. 6-Ethynyl-2-phenyl-8,8a-dihydroindeno[1,2-d]thiazol-3a-ol of melting point 118° C. is obtained.

Example 24 (Compound A77)

2-(3-Chlorophenyl)-6-thiophen-2-yl-8,8a-dihydroindeno[1,2-d]thiazol-3a-ol 5-thiophen-2-yl-indan-1-one This compound is prepared analogously to the process described in Example 1a using thiophene-2-boronic acid; melting point: 148° C.

a) 2-Bromo-5-thiophen-2-ylindan-1-one:

This compound is prepared analogously to the process described in Example 1b using compound 24a; melting point: 114° C.

b) 2-(3-Chlorophenyl)-6-thiophen-2-yl-8,8a-dihydroindeno[1,2-d]thiazol-3a-ol:

This compound is obtained when the compound from Example 24b is reacted with 3-chlorothiobenzamide as described in Example 22. Melting point: 137° C.

TABLE 1

Compounds Synthesized

Formula I

| Example | R1; R1' | R2 | R3 | R4 | Y | X | Salt | m.p. [° C.] |
|---|---|---|---|---|---|---|---|---|
| A01 | 5-NO$_2$; H | H | H | CH$_3$ | — | CH$_2$ | — | 210 |
| A02 | 6-Cl; H | H | H | CH$_3$ | — | CH$_2$ | HCl | 183 |
| A03 | 5-SO$_2$—CH$_3$; H | H | H | CH$_3$ | — | CH$_2$ | HCl | 741 |
| A04 | 7-Cl; H | H | H | CH$_3$ | — | CH$_2$ | — | 132 |
| A05 | 5-Cl; H | H | H | CH$_3$ | — | CH$_2$ | — | 210 |
| A06 | 6-F; H | H | H | CH$_3$ | — | CH$_2$ | — | 132 |
| A07 | 6-(C$_6$H$_5$); H | H | H | CH$_3$ | — | CH$_2$ | HBr | 275 |
| A08 | 6-((C$_6$H$_4$)-3-CF$_3$); H | H | H | CH$_3$ | — | CH$_2$ | HBr | 178 |
| A09 | 6-(thien-3-yl); H | H | H | CH$_3$ | — | CH$_2$ | HBr | 184 |
| A10 | 6-((C$_6$H$_4$)-3-F); H | H | H | CH$_3$ | — | CH$_2$ | HBr | 197 |
| A11 | 6-CN; H | H | H | CH$_3$ | — | CH$_2$ | HBr | 217 |
| A12 | 6-((C$_6$H$_4$)-4-CH$_3$); H | H | H | CH$_3$ | — | CH$_2$ | HBr | 194 |
| A13 | 6-((C$_6$H$_4$)-4-CF$_3$); H | H | H | CH$_3$ | — | CH$_2$ | HBr | 193 |
| A14 | 6-((C$_6$H$_3$)-3,5-di-CF$_3$); H | H | H | CH$_3$ | — | CH$_2$ | HBr | 262 |
| A15 | 6-((C$_6$H$_4$)-3-Cl); H | H | H | CH$_3$ | — | CH$_2$ | HBr | 184 |
| A16 | 6-((C$_6$H$_4$)-3-OCF$_3$); H | H | H | CH$_3$ | — | CH$_2$ | HBr | 212 |
| A17 | 6-((C$_6$H$_4$)-4-Cl); H | H | H | CH$_3$ | — | CH$_2$ | HBr | 190 |
| A18 | 5-C(CH$_3$)$_3$; H | H | H | CH$_3$ | — | CH$_2$ | HBr | 282 |
| A19 | 6-((C$_6$H$_4$)-2-CF$_3$); H | H | H | CH$_3$ | — | CH$_2$ | HBr | 200 |
| A20 | 6-((C$_6$H$_4$)-3-OCH$_3$); H | H | H | CH$_3$ | — | CH$_2$ | HBr | 169 |
| A21 | 6-(naphth-1-yl); H | H | H | CH$_3$ | — | CH$_2$ | HBr | 200 |
| A22 | 7-((C$_6$H$_4$)-4-CF$_3$); H | H | H | CH$_3$ | — | CH$_2$ | HBr | 213 |
| A23 | 5-((C$_6$H$_4$)-4-CF$_3$); H | H | H | CH$_3$ | — | CH$_2$ | HBr | 221 |
| A24 | 6-OCF$_3$; H | H | H | CH$_3$ | — | CH$_2$ | HBr | 219 |
| A25 | 6-Cl; H | CH$_2$—CH$_3$ | H | pyrid-3-yl | — | CH$_2$ | — | 89 |
| A75 | 6-Cl; H | H | H | pyrid-3-yl | — | CH$_2$ | — | 134 |
| A26 | 6-Cl; H | H | H | C$_6$H$_5$ | — | CH$_2$ | — | 165 |
| A27 | 6-Cl; H | CH$_3$ | H | CH$_3$ | — | CH$_2$ | — | 94 |
| A28 | 6-((C$_6$H$_4$)-4-Cl); H | CH$_3$ | H | CH$_3$ | — | CH$_2$ | — | 129 |
| A29 | 6-((C$_6$H$_4$)-3-Cl); H | CH$_3$ | H | CH$_3$ | — | CH$_2$ | — | 81 |
| A30 | 6-Cl; H | H | H | C$_6$H$_4$-3-Cl | — | CH$_2$ | HBr | 207 |
| A31 | 6-Cl; H | H | H | (C$_6$H$_3$)-2,4-di-Cl | — | CH$_2$ | HBr | 225 |
| A32 | 6-Cl; H | H | H | (C$_6$H$_4$)-4-CF$_3$ | — | CH$_2$ | HBr | 226 |
| A33 | 6-Cl; H | H | H | C$_6$H$_5$ | — | CH$_2$ | HCl | 155 |
| A34 | 6-Cl; H | H | H | (C$_6$H$_4$)-4-O-pyrid-2-yl-5-CF3 | — | CH$_2$ | HBr | 235 |
| A35 | 6-Cl; H | H | H | (C$_6$H$_4$)-2-(pyrrol-1-yl) | — | CH$_2$ | — | 140 |
| A36 | 6-Cl; H | H | H | (C$_6$H$_4$)-4- | — | CH$_2$ | — | 144 |

TABLE 1-continued

Compounds Synthesized

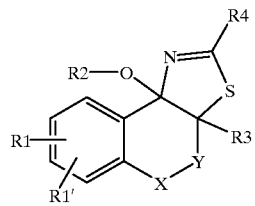

Formula I

| Example | R1; R1' | R2 | R3 | R4 | Y | X | Salt | m.p. [° C.] |
|---|---|---|---|---|---|---|---|---|
| A37 | 6-Cl; H | H | H | OCH$_3$ CH$_2$—CH$_3$ | — | CH$_2$ | HBr | 230 |
| A38 | 6-Cl; H | H | H | pyrid-4-yl | — | CH$_2$ | — | 158 |
| A39 | 5-((C$_6$H$_4$)-4-CF$_3$); H | H | H | CH$_3$ | — | CH$_2$ | — | 215 |
| A40 | 6-Cl; H | H | H | cyclohexyl | — | CH$_2$ | HBr | 170 |
| A41 | 6-Cl; H | H | H | (C$_6$H$_4$)-3-Cl-4-F | — | CH$_2$ | HBr | 255 |
| A42 | 6-C≡CH; H | H | H | C$_6$H$_5$ | — | CH$_2$ | HBr | 134 |
| A43 | 6-CH$_2$—CH$_3$; H | H | H | C$_6$H$_5$ | — | CH$_2$ | HBr | 119 |
| A44 | 6-COOH; H | H | H | C$_6$H$_5$ | — | CH$_2$ | HBr | >300 |
| A45 | 6-Cl; H | H | H | (C$_6$H$_4$)-4-Cl | — | CH$_2$ | — | 142 |
| A46 | 6-Cl; H | H | H | thien-2-yl | — | CH$_2$ | HBr | 211 |
| A47 | 6-O—CH2-CF$_3$; H | H | H | CH$_3$ | — | CH$_2$ | HBr | 215 |
| A48 | 6-O—CH2-CF$_3$; H | H | H | C$_6$H$_5$ | — | CH$_2$ | HBr | 240 |
| A49 | 6-O—((C$_6$H$_4$)-4-Cl); H | H | H | CH$_3$ | — | CH$_2$ | HBr | 226 |
| A50 | 6-O—((C$_6$H$_4$)-4-Cl); H | H | H | C$_6$H$_5$ | — | CH$_2$ | HBr | 237 |
| A51 | 6-O—((C$_6$H$_4$)-3-CH$_3$); H | H | H | CH$_3$ | — | CH$_2$ | HBr | 267 |
| A52 | 6-O—((C$_6$H$_4$)-3-CH$_3$); H | H | H | C$_6$H$_5$ | — | CH$_2$ | HBr | 254 |
| A53 | 6-Cl; H | H | H | (C$_6$H$_4$)-4-OCF$_3$ | — | CH$_2$ | — | 178 |
| A54 | 6-Cl; H | H | H | pyrid-2-yl | — | CH$_2$ | — | 130 |
| A55 | 6-Cl; H | H | H | 2-tert-Butyl-5-methyl-furan-4-yl | — | CH$_2$ | — | 243 |
| A56 | 6-Cl; H | H | H | (C$_6$H$_4$)-3-OCH$_3$ | — | CH$_2$ | — | 142 |
| A57 | 6-Cl; H | H | H | (C$_6$H$_4$)-2-OC$_2$H$_5$ | — | CH$_2$ | — | 140 |
| A58 | 5-tBu; H | H | H | C$_6$H$_5$ | — | CH$_2$ | — | 161 |
| A59 | 5-tBu; H | H | H | (C$_6$H$_4$)-4-Cl | — | CH$_2$ | — | 133 |
| A60 | 5-tBu; H | H | H | CH$_2$—CH$_3$ | — | CH$_2$ | — | 128 |
| A61 | 5-tBu; H | H | H | pyridin-4-yl | — | CH$_2$ | — | 132 |
| A62 | 6-CN; H | H | H | pyridin-4-yl | — | CH$_2$ | — | 140 |
| A63 | 6-CN; H | H | H | CH$_2$—CH$_3$ | — | CH$_2$ | — | 196 |
| A64 | 5-((C$_6$H$_4$)-4-CF$_3$); H | H | H | C$_6$H$_5$ | — | CH$_2$ | — | 161 |
| A65 | 5-((C$_6$H$_4$)-4-CF$_3$); H | H | H | (C$_6$H$_4$)-4-Cl | — | CH$_2$ | — | 172 |
| A66 | 5-((C$_6$H$_4$)-4-CF$_3$); H | H | H | pyridin-4-yl | — | CH$_2$ | — | 218 |
| A67 | 5-((C$_6$H$_4$)-4-CF$_3$); H | H | H | CH$_2$—CH$_3$ | — | CH$_2$ | — | 145 |
| A68 | 6-OCF$_3$; H | H | H | pyridin-4-yl | — | CH$_2$ | — | 134 |
| A69 | 6-OCF$_3$; H | H | H | CH$_2$—CH$_3$ | — | CH$_2$ | — | 110 |
| A70 | 6-C≡CH; H | H | H | C$_6$H$_5$ | — | CH$_2$ | — | 118 |
| A71 | 6-C≡CH; H | H | H | (C$_6$H$_4$)-4-Cl | — | CH$_2$ | — | 136 |
| A72 | 6-C≡CH; H | H | H | pyridin-4-yl | — | CH$_2$ | — | 101 |
| A73 | 6-C≡CH H | H | H | CH$_2$—CH$_3$ | — | CH$_2$ | — | 149 |
| A74 | H; H | H | H | CH$_3$ | — | CH$_2$ | HBr | 273 |
| A76 | 6-(thien-2-yl); H | H | H | C$_6$H$_5$ | — | CH$_2$ | — | 157 |
| A77 | 6-(thien-2-yl); H | H | H | (C$_6$H$_4$)-3-Cl | — | CH$_2$ | — | 138 |
| A78 | 6-Cl; H | H | H | (C$_6$H$_4$)-2-Cl | — | CH$_2$ | — | 145 |
| A79 | 6-(thien-2-yl); H | H | H | (C$_6$H$_4$)-2-Cl | — | CH$_2$ | — | 134 |
| A80 | 6-(thien-2-yl); H | H | H | Pyridin-4-yl | — | CH$_2$ | — | 151 |
| A81 | 5-(C$_6$H$_3$-3,5-di-Cl) | H | H | Pyridin-4-yl | — | CH$_2$ | — | 140 |
| A82 | 5-(C$_6$H$_3$-3,5-di-Cl) | H | H | (C$_6$H$_4$)-3-Cl | — | CH$_2$ | — | 156 |
| A83 | 5,6-di-CH$_3$; H | H | H | CH$_3$ | — | CH$_2$ | — | 274 |
| A84 | 5,6-di-CH$_3$; H | H | H | C$_6$H$_5$ | — | CH$_2$ | — | 282 |
| A85 | 6-Cl; H | H | H | CH$_2$-1H-indol-3-yl | — | CH$_2$ | — | 121 |
| A86 | 6-Cl; H | H | H | CH$_2$-1H-indol-3-yl-5-OH | — | CH$_2$ | — | 260 |
| A87 | 6-Cl; H | H | H | (C$_6$H$_4$)-2-OH | — | CH$_2$ | — | 146 |
| A88 | 6-Cl; H | H | H | (C$_6$H$_4$)-4-OH | — | CH$_2$ | — | 220 |
| A89 | 6-Cl; H | H | H | (C$_6$H$_4$)-3-OH | — | CH$_2$ | — | 119 |

TABLE 1-continued

Compounds Synthesized

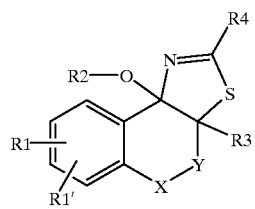

Formula I

| Example | R1; R1' | R2 | R3 | R4 | Y | X | Salt | m.p. [° C.] |
|---|---|---|---|---|---|---|---|---|
| A90 | 6-CN; H | H | H | CH$_2$-1H-indol-3-yl | — | CH$_2$ | — | 130 (dec.) |
| A91 | 6-C≡CH; H | H | H | CH$_2$-1H-indol-3-yl | — | CH$_2$ | — | 120 (dec.) |
| A92 | 6-(C$_6$H$_4$)-3-CF$_3$; H | H | H | CH$_2$-1H-indol-3-yl | — | CH$_2$ | — | 140 (dec.) |

Example 25: Effects on Lipid Metabolism

The efficacies of the compounds were tested as follows:
Biological Test Model:

The anorectic action was tested on male NMRI mice. After withdrawal of feed for 24 hours, each test preparation was administered via a stomach tube. The animals were kept individually with free access to drinking water and were offered evaporated milk 30 minutes after receiving the preparation. The consumption of evaporated milk was determined half-hourly for 7 hours and the general conditions of the animals were observed.

The measured milk consumptions were compared with that of the untreated control animals.

Results are shown in Table 2, which indicates anorectic action, measured as the reduction of the cumulated milk consumption of treated animals in comparison to the untreated animals. It can be inferred from Table 2 that the compounds of the formula I exhibit a very good anorectic action.

TABLE 2

|  | Oral dose [mg/kg] | Number of animals/cumulated milk consumption of the treated animals N/[ml] | Number of animals/cumulated milk consumption of the untreated animals N/[ml] | Reduction of the cumulated milk consumption in % of the control |
|---|---|---|---|---|
| Example A08 | 50 | 12/0.22 | 12/2.48 | 91 |
| Example A14 | 50 | 5/0.8 | 5/3.92 | 80 |
| Example A16 | 50 | 5/0.84 | 5/4.2 | 79 |
| Example A22 | 50 | 5/1.58 | 5/5.42 | 71 |
| Example A23 | 50 | 5/0.6 | 5.5.42 | 89 |
| Example A75 | 25 | 5/2.30 | 5/4.02 | 43 |
| Example A25 | 50 | 5/1.12 | 5/3.44 | 67 |
| Example A26 | 50 | 5/0.2 | 5/4.02 | 95 |
| Example A33 | 50 | 5/0.24 | 5/4.32 | 94 |
| Example A27 | 50 | 5/1.14 | 5/4.50 | 75 |
| Example A30 | 50 | 5/0.42 | 5/3.98 | 89 |
| Example A31 | 50 | 5/0.2 | 5/3.98 | 95 |
| Example A37 | 50 | 5/0.36 | 5/5.70 | 94 |
| Example A38 | 50 | 5/0.28 | 5/4.12 | 93 |
| Example A39 | 50 | 5/1.06 | 5/4.0 | 73 |
| Example A40 | 50 | 5/0.62 | 4/3.53 | 82 |
| Example A42 | 50 | 5/1.08 | 5/4.04 | 73 |
| Example A45 | 50 | 5/0.34 | 5/4.38 | 92 |
| Example A48 | 50 | 5/0.40 | 5/3.80 | 89 |
| Example A49 | 50 | 5/0.74 | 5/3.30 | 78 |
| Example A62 | 50 | 5/1.40 | 5/4.54 | 69 |
| Example A70 | 50 | 5/1.06 | 5/4.82 | 78 |
| Example A77 | 50 | 5/1.56 | 5/4.32 | 64 |

We claim:
1. A compound of the formula I

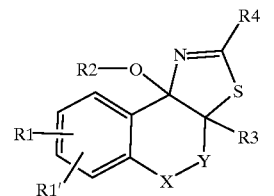

in which
Y is a direct bond, —CH$_2$—, or —CH$_2$—CH$_2$—;
X is CH$_2$, CH(CH$_3$), CH(C$_2$H$_5$), (C$_3$H$_7$), or CH(C$_6$H$_5$):
R1, R1' independently of one another are selected from the group consisting of H, F, Cl, Hr, I, CF$_3$, NO$_2$, CN, COOH, COO(C$_1$–C$_6$)alkyl, CONH, CONH(C$_1$–C$_6$) alkyl, CON[(C$_1$–C$_6$)alkyl]$_2$, (C$_1$–C$_6$)-alkyl, (C$_2$–C$_6$)-alkenyl, (C$_2$–C$_6$)-alkynyl, and O—(C$_1$–C$_6$)-alkyl, wherein optionally one or more of the hydrogens in the alkyl radicals is replaced by an alternative substituent selected from the group consisting of F, OH, OC(O)CH$_3$, OC(O)H, OCH$_2$Ph, NH$_2$, NH—CO—CH$_3$ or N(COOCH$_2$Ph)$_2$; SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, and SO$_2$—(CH$_2$)$_n$-phenyl, wherein n is 0–6 and the phenyl radical is optionally substituted up to two times by a substituent selected from the group consisting of F, Cl, Br, OH, CF$_3$, NO$_2$, CN, OCF$_3$, O—(C$_1$–C$_6$)-alkyl, (C$_1$–C$_6$)-alkyl, NH$_2$; NH$_2$, NH—(C$_1$–C$_6$) alkyl, N((C$_1$–C$_6$)-alkyl)$_2$, NH(C$_1$–C$_7$)-acyl, phenyl, biphenyl, and O—(CH$_2$)$_n$ phenyl, wherein n is 0–6, 1- or 2-naphthyl, 2-, 3- or 4-pyridyl, 2 or 3-furanyl or 2- or 3-thienyl, and wherein the phenyl, biphenyl, naphthyl, pyridyl, furanyl or thienyl rings each is optionally substituted one to 3 times by an alternative substituent selected from the group consisting of F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$ C$_6$) alkyl, N((C$_1$–C$_6$)-alkyl)$_2$, SO$_2$—CH$_3$, COOH, COO—(C$_1$–C$_6$)-alkyl, and CONH$_2$; 1,2,3 triazol-5-yl, wherein the triazole ring is optionally substituted in the 1-, 2- or 3-position by methyl or benzyl; and tetrazol-5-yl, wherein the tetrazole ring is optionally substituted in the 1- or 2-position by methyl or benzyl;
R2 is H, (C$_1$–C$_6$)-alkyl, (C$_3$–C$_6$)-cycloalkyl, (CH$_2$)$_{n1}$-phenyl, (CH$_2$)$_{n1}$-thienyl, (CH$_2$)$_{n1}$-pyridyl, (CH$_3$)$_{n1}$-furyl, C(O)—(C$_1$–C$_6$)-alkyl, (C(O)—(C$_3$–C$_6$)-cycloalkyl, C(O)—(CH$_2$)$_{n1}$-phenyl, C(O)—(CH$_2$)$_{n1}$-thienyl, C(O)—(CH$_2$)$_{n1}$-pyridyl C(O)—(CH$_2$)$_{n1}$-furyl, wherein n1 is 0–5 and in which phenyl, thienyl, pyridyl, furyl each is optionally substituted up to two times by a substituent selected from the group consisting of Cl, F, CN, CF$_3$, (C$_1$–C$_3$)-alkyl, OH, and O—(C$_1$–C$_6$)-alkyl;
R3 is H, (C$_1$–C$_6$)-alkyl, F, CN, N$_3$, O—(C$_1$–C$_6$)-alkyl, (CH$_2$)$_{n1}$-phenyl, (CH$_2$)$_{n1}$-thienyl, (CH$_2$)$_{n1}$-pyridyl, or (CH$_2$)$_{n1}$-furyl, wherein n1 is 0–5 and in which phenyl, thienyl, pyridyl, furyl each is optionally substituted up to two times by one of two substituents selected from the group consisting of Cl, F, CN, CF$_3$, (C$_1$–C$_3$)-alkyl, OH, O—(C$_1$–C$_6$)-alkyl; (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$, and OC(O)CH$_3$;

R4 is (C$_1$ C$_8$) allyl, (C$_3$–C$_7$)-cycloalkyl, (C$_2$–C$_6$)-alkenyl, (C$_2$–C$_6$)-alkynyl, or (C$_4$–C$_7$)-cycloalkenyl, wherein one or more hydrogens in the alkyl radical may be replaced by F and one hydrogen in the alkyl radical may be replaced by a substituent selected from the group consisting of OH, OC(O)CH$_3$, OC(O)H, O—CH$_2$—Ph (or) and O—(C$_1$–C$_4$)-alkyl; (CH$_2$)$_{n2}$—NR6R7, wherein n2 is 1–6 and R6 and R7 independently of one another are selected from the group consisting of H, (C$_1$–C$_6$)-alkyl, (C$_3$–C$_6$)-cycloalkyl, CO—(C$_1$–C$_6$)-alkyl, CHO, and CO-phenyl, or wherein-NR6R7 is a ring; (CH$_2$)$_n$-aryl, wherein n is 0–6 and aryl is selected from the group consisting of phenyl, biphenyl, 1- or 2-naphthyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoazolyl, 2- or 3-pyrrolyl, 2- or 3-pyridazinyl, 2-, 4- or 3-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl and N-methyl-imidazol-2-, -4- or -5-yl and the aryl radical or heteroaryl radical is optionally substituted up to two times by a substituent selected from the group consisting of F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$ C$_6$)alkyl, CON[(C$_1$–C$_6$)alkyl]$_2$, CONH(C$_3$–C$_6$) cyclo-alkyl, NH$_2$, NH—CO—(C$_1$–C$_6$)-alkyl, NH—CO-phenyl, pyrrolidin-1-yl, morpholin-1-yl, piperidin-1-yl, piperazin 1 yl, 4-methylpiperazin-1-yl, (CH$_2$)$_{n3}$-phenyl, O—(CH$_2$)$_{n3}$-phenyl, S-(CH$_2$)$_{n3}$-phenyl, and SO$_2$—(CH$_2$)$_{n3}$-phenyl, wherein n3 =0–3, or a physiologically tolerable salt of the compound.

2. A compound of the formula I as claimed in claim 1, wherein Y is a direct bond and X is CH$_2$ or a physiologically tolerable salt of the compound.

3. A compound of the formula I as claimed in claim 2, wherein R3 is H or F; or a physiologically tolerable salt thereof.

4. A compound of the formula I as claimed in claim 2, wherein
R1, R1' independently of one another are selected from the group consisting of H, F, Cl, Br, NO$_2$, CN, COOH, (C$_1$–C$_6$)-alkyl, (C$_2$–C$_6$)-alkenyl, (C$_2$–C$_6$)-alkynyl, O—(C$_1$–C$_6$)-alkyl, OCF$_3$, OCH$_2$CF$_3$, phenyl, O—(CH$_2$)$_n$-phenyl, wherein n is 0–6, 1- or 2-naphthyl, and 2- or 3-thienyl, wherein the phenyl, naphthyl or thienyl rings each is optionally substituted one to 3 times by an alternative substituent selected from the group consisting of F, Cl, Br, I, OH, CF$_3$, NO$_2$, CN, OCF$_3$, O—(C$_1$–C$_6$)-alkyl, (C$_1$–C$_6$)-alkyl, and NH$_2$;
R2 is H, (C$_1$–C$_6$)-alkyl, ($_3$–C$_6$)-cycloalkyl, or (CH$_2$)$_{n1}$ phenyl, wherein n1 is 0–5;
R3 is H, or F;
R4 is (C$_1$–C$_3$)-alkyl, (C$_3$–C$_7$) cycloalkyl, (CH$_2$)$_{n2}$—NR6R7, wherein n2 is 1–6 and R6 and R7 each is selected from the group consisting of H, (C$_1$–C$_6$)-alkyl, or form a ring selected from the group consisting of pyrrolidine, piperidine, morpholine, piperazine, N4-methylpiperazin-1-yl, N4-benzylpiperazin 1-yl, and phthalimidoyl; (CH$_2$)$_n$-aryl, wherein n is 0–6 and aryl is selected from the group consisting of phenyl, biphenyl, 1- or 2-naphthyl, 2-, 3- or 1-pyridyl, 2- or 3-thienyl, 2- or 3-furyl, 2-, -4- or 5-thiazolyl, 2-, 4- or 5-oxazolyl, 1-pyrazolyl, 3- or 5-soxazolyl, 2- or 4-pyrrolyl, 2- or 3-pyridazinyl, 2, -4- or 5-pyrimidiniyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol 3 yl, indol-5-yl, and N-methylimidazol-2-, -4- or -5-yl and the aryl radical or heteroaryl radical is optionally substituted up to two times by a substituent selected from the group consisting of F, Cl, Br, OH, $CF_3$, $NO_2$, CN, $OCF_3$, $O-(C_1-C_6)$-alkyl, pyrrolidin-1-yl, morpholin-1-yl, piperidin-1-yl, piperazin 1 yl, and 4-methylpiperazin-1-yl; or a physiologically tolerable salt thereof.

5. A compound of the formula I as claimed in claim 1, wherein

Y is a direct bond;

X is $CH_2$,

R1 is Cl;

R1' is H;

R2 is H;

R3 is H;

R4 is phenyl;

or a physiologically tolerable salt thereof.

6. A compound of the formula I as claimed in claim 1, wherein —NR6R7 is a ring selected from the group consisting of pyrrolidine, piperidine, morpholine, piperazine, N-4-methylpiperazin-1-yl, N-4-benzylpiperazin-1-yl, and phthalimidoyl.

7. A pharmaceutical composition comprising at least one compound as claimed in claim 1.

8. A pharmaceutical composition as claimed in claim 7, further comprising at least one slimming preparation.

9. A process for the production of a pharmaceutical composition, the pharmaceutical composition comprising at least one compound as claimed in claim 1, the process comprising mixing the compound with a pharmaceutically suitable vehicle.

10. A method of treatment of obesity in a patient, comprising providing a medicament that comprises a compound as claimed in claim 1 to the patient.

11. A method of treatment of type II diabetes in a patient, comprising providing a medicament that comprises a compound as claimed in claim 1 to the patient.

* * * * *